United States Patent [19]
Sauer et al.

[11] Patent Number: 5,852,219
[45] Date of Patent: Dec. 22, 1998

[54] CATALYST, PROCESS FOR ITS PREPARATION, AND USE FOR SYNTHESIS OF METHYL MERCAPTAN

[75] Inventors: Joerg Sauer, Rodenbach; Wolfgang Boeck, Langenselbold; Lukas von Hippel, Alzenau; Werner Burkhardt, Brachttal; Stephan Rautenberg, Hanau; Dietrich Arntz, Oberursel; Willi Hofen, Rodenbach, all of Germany

[73] Assignee: Degussa Aktiengesellschaft, Frankfurt am Main, Germany

[21] Appl. No.: 885,045

[22] Filed: Jun. 30, 1997

[30] Foreign Application Priority Data

Sep. 26, 1996 [DE] Germany ............... 196 39 584.4

[51] Int. Cl.$^6$ .................................................. C07C 319/08
[52] U.S. Cl. ............................. 568/71; 502/305; 423/606
[58] Field of Search ........................... 502/305; 423/606; 568/71

[56] References Cited

U.S. PATENT DOCUMENTS

| | | | |
|---|---|---|---|
| 2,820,062 | 1/1958 | Folkins et al. | 260/609 |
| 4,908,343 | 3/1990 | Bhasin | 502/218 |
| 5,057,481 | 10/1991 | Bhasin | 502/208 |

OTHER PUBLICATIONS

Patent Abstract of Japan 56–105750A, Nov. 1981.

Mashkina et al., "Activity of Tungstate Catalysts in the Synthesis of Methyl Mercaptane from Methanol and Hydrogen Sulfide", Reaction Kinet. Catalyst Letter, vol. 36, No. 1, 159–164, 1988.

World pat index acc No. 81–72936d abs of JP56105750, Aug. 1981.

*Primary Examiner*—Gary Geist
*Assistant Examiner*—Jean F. Vollano
*Attorney, Agent, or Firm*—Beveridge, DeGrandi, Weilacher & Young, L.L.P.

[57] ABSTRACT

A catalyst for the synthesis of methyl mercaptan from hydrogen sulfide and methanol, as well as a process for preparing the catalyst. The catalyst contains active aluminum oxide on which 15% to 40% by weight cesium tungstate is deposited as the activator. The activator, cesium tungstate, gives an unexpected increase in activity and selectivity as compared with potassium tungstate, which is used exclusively at the present state of the art.

12 Claims, No Drawings

CATALYST, PROCESS FOR ITS PREPARATION, AND USE FOR SYNTHESIS OF METHYL MERCAPTAN

INTRODUCTION AND BACKGROUND

The present invention relates to a catalyst for synthesis of methyl mercaptan from methanol and hydrogen sulfide, and a process for preparing this catalyst. In a further aspect, the present invention relates to a process for the synthesis of methyl mercaptan from methanol and hydrogen sulfide using the new catalyst of the invention.

Methyl mercaptan is an important industrial intermediate for synthesis of methionine and for production of dimethyl sulfoxide and dimethyl sulfone. At present, it is made predominantly from methanol and hydrogen sulfide by reaction in the presence of an aluminum oxide catalyst. Methyl mercaptan is usually synthesized in the gas phase at temperatures of 300° to 500° C. and pressures of 1 to 25 bar.

Aside from the methyl mercaptan produced, the reaction gas mixture contains unreacted starting materials and byproducts such as dimethyl sulfide and dimethyl ether as well as gases which are inert in this reaction, such as methane, carbon monoxide, hydrogen and nitrogen. The methyl mercaptan which is produced is separated from this reaction mixture.

If the reaction of hydrogen sulfide and methanol is carried out in the presence of the catalyst at elevated pressure, and the product is at elevated pressure (greater than 7 bar), methyl mercaptan can be separated, for example, by washing with methanol at a washer head temperature of 25° C., as described in German Patent 17 68 826. If the product is at standard pressure, the recovery has to be done at temperatures down to -60° C. (Japanese Laid-Open Patent Application 45-10728) to obtain the methyl mercaptan in liquid form. The unreacted hydrogen sulfide can be returned to the reactor, as described in German Patent 17 68 826.

The highest possible selectivity is required in the catalytic reaction of methanol and hydrogen sulfide to produce methyl mercaptan, so as to keep the cost of separating the methyl mercaptan produced as low as possible, for the process to be economically feasible. Here the cost of energy for cooling the reaction gas mixture to condense the methyl mercaptan is a major cost factor.

The aluminum oxide catalyst is usually activated by doping with potassium tungstate to increase its activity and selectivity. The activator is usually used in proportions of up to 15% of the total weight of the catalyst. The activity and selectivity can also be improved by increasing the molar ratio of hydrogen sulfide to methanol. Usually molar ratios of 1 to 10 are used.

A high molar ratio, of course, means that the hydrogen sulfide is in great excess in the reaction gas mixture, so that large volumes of gas must be recirculated. The ratio of hydrogen sulfide to methanol should be only slightly different from 1 to reduce the cost of energy for recirculation. It is also desirable to carry out the reaction at the lowest possible temperature to reduce heat loss from the reactor.

U.S. Pat. No. 2,820,062 describes a process for producing organic thiols using an activated aluminum oxide catalyst which has been activated with potassium tungstate in proportions of 1.5% to 15% by weight, based on the weight of the catalyst. This catalyst gives good activities and selectivities at a reaction temperature of 400° C. and a molar ratio of 2. This US Patent mentions various possibilities for incorporating the potassium tungstate into the aluminum oxide, including impregnation processes, coprecipitations, and simple mixtures. The actual catalyst production is considered of little importance to the economics of the process for methyl mercaptan synthesis.

An object of this invention is to improve activity and selectivity of a catalyst used for methyl mercaptan synthesis compared with the known catalysts, and which thus leads to improved economics for the process. A further object of the invention to use low molar ratios of hydrogen sulfide to methanol in the synthesis of methyl mercaptan.

SUMMARY OF THE INVENTION

These and other objects are attained by a catalyst comprising aluminum oxide as support containing an alkali tungstate as the activator. The catalyst is characterized by the fact that the activator is cesium tungstate, which is used in a proportion of from more than 15% to 40%, preferably 20% to 35% by weight, based on the total weight of the finished catalyst.

It was found that cesium tungstate gives the catalyst improved activity with simultaneously improved selectivity, in comparison with potassium tungstate, which is solely used in the state of the art. These improved production data are achieved only at significantly higher concentrations of the activator used according to the invention than for the conventional activator, potassium tungstate. Cesium tungstate exhibits no advantages over potassium tungstate at concentrations below 15% by weight. Although potassium tungstate gives no further improvements in catalyst characteristics with increasing concentration, use of cesium tungstate unexpectedly shows improvement in activity and selectivity up to a concentration greater than 25% by weight. No further significant improvements in characteristics are obtained if the upper concentration limit of 40% by weight is exceeded.

DETAILED DESCRIPTION OF INVENTION

In carrying out the invention, so-called "active aluminum oxide" is used as the aluminum oxide for this catalyst. This material has high specific surface area of 10 to 400 m$^2$/g, and consists primarily of oxides from the transitional series of the crystallographic phases of aluminum oxide (see, for instance, Ullmann's Encyclopedia of Industrial Chemistry, 1985, Vol. A1, pages 561–562). These transitional oxide phases include χ, κ, γ, δ, η, and θ aluminum oxide. All of these crystallographic phases convert to the thermally stable α-aluminum oxide when the aluminum oxide is heated to temperatures above 1100° C.

Active aluminum oxide is sold commercially in various qualities and physical forms for catalytic applications. Particles in the form of granulated or extruded aluminum oxide with particle diameters of 1 to 5 mm, specific surface areas of 180–400 m$^2$/g, total pore volumes of 0.3 to 1.0 ml/g, and bulk densities of 300–900 g/liter are quite suited to the purpose. Aluminum oxide having a specific surface area greater than 200 m$^2$/g is preferred for the purpose of the invention, as the catalytic activity of the finished catalyst increases slightly as the surface of the aluminum oxide increases.

The aqueous impregnating solution of cesium tungstate can be produced simply from commercial tungstic acid ($H_2WO_4$) and cesium hydroxide ($CsOH.H_2O$). That is done by suspending tungstic acid in water and dissolving it by adding a base and heating. Cesium hydroxide is also dissolved in water, separately from the tungstic acid. Then the two solutions are combined. The pH of the finished impregnating solution should be in the alkaline range of 8 to 14 to stabilize the solution. No clear solution can be obtained without that.

Both organic and inorganic bases are suitable for stabilizing the impregnating solution. Bases which can be driven off, without a residue, by a final heat treatment of the catalyst are preferred. These bases include ammonium hydroxide and organic bases, such as various amines.

Before applying the impregnating solution, it is desirable to free the aluminum oxide moldings of adsorbed water and other volatile impurities by calcining at temperatures of 250° to 600° C. for 1 to 10 hours, preferably 2 to 6 hours. Such pretreatment is not absolutely necessary, though.

Various impregnation methods such as immersion, spraying, and pore volume impregnation can be used in one or more steps to apply the cesium tungstate. The impregnation process selected needs only to make it possible to apply the desired high loading proportion evenly over the whole cross-sectional area of the aluminum oxide moldings. The evenness of the impregnation can also be improved by slow predrying of the impregnated aluminum oxide for several hours at room temperature.

Cesium tungstate is preferably applied to the particles in a single step by pore volume impregnation. After predrying for 2 to 20 hours at room temperature, the initial concentration gradient across the cross section of the particles is largely evened out. Then the catalyst precursors thus obtained are calcined at 300° to 600° C. for 1 to 10 hours. That fixes the cesium tungstate to the aluminum oxide, and decomposes and drives off the base of the impregnating solution.

To prevent damage to the catalyst by too rapid removal of the residual moisture, the temperature, after predrying, should be increased slowly from room temperature to the final calcination temperature. Alternatively, one can use a separate intermediate drying at 100° to 200° C. for about 0.5 to 4 hours.

Two different types of aluminum oxide were used for the following examples. Their properties are shown in Table I, below.

TABLE 1

Properties of aluminum oxide

|  | Aluminum oxide I | Aluminum oxide II |
| --- | --- | --- |
| Manufacturer | Norton | Rhône-Poulenc |
| Type | SA 6276 | Spheralite 501a |
| Specific surface area | 200 m$^2$/g | 320 m$^2$/g |
| Bulk density | 420–590 g/liter | 800 g/liter |
| Pore volume | 0.9–1 ml/g | 0.45 ml/g |
| Water uptake | 90 g/100 g Al$_2$O$_3$ | 52 g/100 g Al$_2$O$_3$ |
| Granule diameter | 3 mm | 3 mm |

COMPARISON EXAMPLE 1

1 kg aluminum oxide I was impregnated with 8% by weight potassium tungstate, using pore volume impregnation. The details of the process were as follows:

The aluminum particles were first calcined in air for 4 hours at 455° C.

The potassium tungstate solution was made by suspending 66.6 g tungstic acid in 500 ml water and dissolving 29.9 g potassium hydroxide in 450 ml water. The two components were mixed and heated to 95° C. with stirring. A clear solution formed. The solution was sprayed over granules in a rotating coating pan. The volume of the impregnating solution was about 110% of the experimentally determined water uptake of the particles used.

The impregnated granules were kept for 16 hours in air, and then heated for 2 hours at 160° C. to remove the residual moisture. Then the granules were calcined in air for 4 hours at 455° C.

COMPARISON EXAMPLE 2

Comparison Example 1 was repeated, except that the aluminum particles were charged with 16% by weight potassium tungstate. To do so, the starting quantities of tungstic acid and potassium hydroxide were increased appropriately.

COMPARISON EXAMPLE 3

1 kg aluminum oxide II was charged, as in Comparison Example 1, with 8% by weight potassium tungstate, based on the total weight of the impregnated aluminum oxide.

In this process, 66.6 of tungstic acid was suspended in 400 ml water. 29.9 g potassium hydroxide was dissolved in 170 ml water. The two components were stirred together with heating to 95° C., forming a clear solution. Because of the lower pore volume of aluminum oxide II, the volume of this impregnating solution was about 110% of the experimentally determined water uptake of the granulate used.

COMPARISON EXAMPLE 4

Comparison Example 3 was repeated, except that the aluminum particles were charged with 16% by weight potassium tungstate. To do so, the starting quantities of tungstic acid and potassium hydroxide were increased appropriately.

COMPARISON EXAMPLE 5

Comparison Example 4 was repeated with the charge of potassium tungstate increased to 20% by weight.

COMPARISON EXAMPLE 6

Aluminum oxide II was charged with a total of 16% by weight potassium tungstate in a two-step impregnation. An excess of impregnating solution was used in the first impregnation step. The second impregnation step was done by pore volume impregnation.

The details of the process were as follows: 1 kg aluminum oxide II was calcined in air for 4 hours at 455° C. A prepared solution of 8.7% by weight potassium tungstate in water at a temperature of 95° C. was poured over the granules in a vessel until all the catalyst particles were covered. After 40 minutes, the excess water was poured off. The wet catalyst particles were predried in air at room temperature and then for 2 hours at 120° C. This treatment deposited 7% by weight potassium tungstate, i. e., 75 g, on the catalyst particles.

For the pore volume impregnation, 115.2 g potassium tungstate was dissolved in 520 ml water, equivalent to 100% of the measured water uptake capability of the catalyst material, at a temperature of 95° C. This solution was distributed over the granulation in a rotating coating pan. That was followed by 16 hours of predrying in air and then two hours drying at 110° C. Finally, the catalyst particles were calcined in air for 4 hours at 455° C.

COMPARISON EXAMPLE 7

1 kg aluminum oxide II was impregnated with 8% by weight cesium tungstate as in the procedure of Comparison Example 3.

That was done by suspending 42.3 g tungstic acid in 400 ml water and dissolving 56.9 g CsOH.H$_2$O in 170 ml water. The two solutions were mixed and heated with stirring to 65° C., at which point a slightly cloudy solution formed. It was impossible to heat the solution to 95° C. as in the case of potassium tungstate because the solution produces a precipitate at higher temperatures.

Impregnation, holding and calcining were done as in the two preceding comparison examples.

EXAMPLE 1

1 kg aluminum oxide II was charged with 20% by weight cesium tungstate. To do so, 121.6 g tungstic acid was suspended in 140 ml water and completely dissolved by adding 260 ml 25% 5 ammonia solution and heating to 50° C. 163.5 g CsOH.H$_2$O was dissolved in 170 ml water and mixed with the first solution.

Precalcining, impregnating, drying, and final calcining were done as in the previous examples.

EXAMPLES 2 and 3

Example 1 was repeated with 25% and 30% charge of cesium tungstate on the aluminum oxide.

APPLICATION EXAMPLE

The catalysts were tested to determine their characteristics in the synthesis of methyl mercaptan from hydrogen sulfide and methanol.

The synthesis was performed in a stainless steel tube having an inside diameter of 14 mm and a length of 500 mm. The catalyst bed, 32.4 ml in each case, was held in place in the reaction tube by inert packings of glass beads at both ends. The reaction tube was heated electrically to the reaction temperature of about 350° C.

The product methyl mercaptan, dimethyl sulfide, dimethyl ether, and unreacted methanol were washed out of the gas current, after it was cooled, with methanol at 25° C., and worked up by distillation.

The test conditions are shown in the following list:
GHSV: 1280 hr$^{-1}$ (based on standard conditions)
LHSV: 0.56 hr$^{-1}$ (based on liquid MeOH)
Reaction temperature: 300°–400° C.
Molar ratio: H$_2$S/MeOH: 1.5
Pressure: 9 bar Table 2 shows the measurements from on-line gas chromatography of the reaction gas mixture and the compositions of the catalysts tested. The reaction temperature required for 90% methanol conversion, T$_{90}$%, was determined as the measure of catalyst activity. Table 2 also shows the selectivity obtained at that operating point.

TABLE 2

Test results for 90% methanol conversion

| Catalyst | Aluminum oxide | Activator | Charge (% by weight) | T$_{90\%}$ (°C.) | Selectivity (%) |
|---|---|---|---|---|---|
| VB1 | I | K$_2$WO$_4$ | 8 | 360 | 79.8 |
| VB2 | I | K$_2$WO$_4$ | 16 | 382 | 86.8 |
| VB3 | II | K$_2$WO$_4$ | 8 | 347 | 79.9 |
| VB4 | II | K$_2$WO$_4$ | 16 | 357 | 89.2 |
| VB5 | II | K$_2$WO$_4$ | 20 | 365 | 91.5 |
| VB6*) | II | K$_2$WO$_4$ | 16 | 357 | 91.3 |

TABLE 2-continued

Test results for 90% methanol conversion

| Catalyst | Aluminum oxide | Activator | Charge (% by weight) | T$_{90\%}$ (°C.) | Selectivity (%) |
|---|---|---|---|---|---|
| VB7 | II | Cs$_2$WO$_4$ | 8 | 323 | 73.6 |
| B1 | II | Cs$_2$WO$_4$ | 20 | 345 | 87.2 |
| B2 | II | Cs$_2$WO$_4$ | 25 | 349 | 92.0 |
| B3 | II | Cs$_2$WO$_4$ | 32.5 | 353 | 92.2 |

VB1: Catalyst according to Comparison Example 1
*): Two-stage impregnation

As the results in Table 2 show, the activity of the catalyst improves when an aluminum oxide with higher specific surface area is used. The selectivity also improves, to a lesser extent. Increasing the potassium tungstate charge from 8% to 16% by weight reduces the activity of the catalyst, but it very decisively improves its selectivity. A further increase in the charge to 20% by weight further reduces the activity. The selectivity increases only slightly, so that catalysts with more than 16% by weight potassium tungstate do not allow improved economics in methyl mercaptan production. Similar behavior was also expected for charging with cesium tungstate. Surprisingly though, catalysts activated with cesium tungstate exhibit substantially improved activity with simultaneously good selectivity. The selectivity can be increased to 92% by raising the charge to more than 20% by weight without the activity being disproportionately reduced.

The discussions above were limited to problems in the synthesis of methyl mercaptan. It will be clear to one skilled in the art, though, that the catalyst according to the invention is likewise suitable for synthesis of mercaptans in general by catalytic reaction of olefinic hydrocarbons with hydrogen sulfide.

Further variations and modifications of the foregoing will be apparent to those skilled in the art and are intended to be encompassed by the claims appended hereto.

German priority application 196 39 584.4 is relied on and incorporated herein by reference.

We claim:

1. A catalyst composition comprising aluminum oxide particles containing cesium tungstate as the activator, wherein the cesium tungstate is present in a proportion of from more than 15% to 40% by weight, based on the total weight of the finished catalyst.

2. The catalyst according to claim 1 wherein the aluminum oxide has a specific surface area from 180 to 400 m$^2$/g.

3. The catalyst according to claim 1 wherein said proportion is 20% to 35% by weight.

4. The catalyst according to claim 2 wherein said aluminum oxide has a total pore volume of 0.3 to 1.0 ml/g.

5. The catalyst according to claim 2 wherein said aluminum oxide has a bulk density of 300 to 900 g/liter.

6. The catalyst according to claim 1 wherein the proportion is 16% to 40% by weight.

7. A process for preparing the catalyst according to claim 1 comprising:
   a) impregnating aluminum oxide particles with an aqueous alkaline solution of cesium tungstate to produce a catalyst precursor,
   b) drying the catalyst precursor at room temperature and
   c) calcining for 2 to 10 hours at temperatures of 300° to 500° C.

8. The process according to claim 7 further comprising suspending tungstic acid in water and dissolving by adding base and heating to produce said aqueous alkaline solution of cesium tungstate, separately dissolving cesium hydroxide in water to produce a solution thereof, combining said solutions and adjusting the pH to 8 to 14 to produce a clear solution.

9. The process according to claim 7 wherein impregnating aluminum oxide is done by immersion, spraying or pore volume impregnation in one or more steps to apply the desired high loading proportion evenly over the whole cross-sectional area of the aluminum oxide particles.

10. The process according to claim 9 wherein drying is carried out after impregnating at 2 to 20 hours at room temperature to even out the concentration gradient across the cross section of the particles.

11. A process for the synthesis of an alkyl mercaptan comprising reacting an alkanol and hydrogen sulfide in the presence of the catalyst of claim 1.

12. The process according to claim 11 for the synthesis of methyl mercaptan wherein methanol and hydrogen sulfide are reacted together.

* * * * *